United States Patent
Anderheggen et al.

(10) Patent No.: US 9,789,052 B2
(45) Date of Patent: Oct. 17, 2017

(54) POLYMER-CONTAINING TRANSPARENT BLEACHING COMPOSITIONS WITH PROTEINS AND/OR SILICONE OILS

(71) Applicant: Henkel AG & Co. KGaA, Duesseldorf (DE)

(72) Inventors: Bernd Anderheggen, Moenchengladbach (DE); Frank Janssen, Cologne (DE)

(73) Assignee: Henkel AG & Co. KGaA (DE)

(*) Notice: Subject to any disclaimer, the term of this patent is extended or adjusted under 35 U.S.C. 154(b) by 0 days.

(21) Appl. No.: 14/937,977

(22) Filed: Nov. 11, 2015

(65) Prior Publication Data

US 2016/0058687 A1  Mar. 3, 2016

Related U.S. Application Data

(63) Continuation of application No. PCT/EP2014/051681, filed on Jan. 29, 2014.

(30) Foreign Application Priority Data

May 16, 2013  (DE) ........................ 10 2013 209 100

(51) Int. Cl.
| | | |
|---|---|---|
| *A61Q 5/08* | (2006.01) | |
| *A61K 8/891* | (2006.01) | |
| *A61K 8/73* | (2006.01) | |
| *A61K 8/81* | (2006.01) | |
| *A61K 8/898* | (2006.01) | |
| *A61K 8/22* | (2006.01) | |
| *A61K 8/23* | (2006.01) | |

(52) U.S. Cl.
CPC ................ *A61K 8/891* (2013.01); *A61K 8/22* (2013.01); *A61K 8/23* (2013.01); *A61K 8/731* (2013.01); *A61K 8/8147* (2013.01); *A61K 8/8152* (2013.01); *A61K 8/898* (2013.01); *A61Q 5/08* (2013.01); *A61K 2800/882* (2013.01)

(58) Field of Classification Search
None
See application file for complete search history.

(56) References Cited

U.S. PATENT DOCUMENTS

| | | | |
|---|---|---|---|
| 7,534,272 B2 | 5/2009 | Cassier et al. | |
| 2005/0008591 A1* | 1/2005 | Nocker | A61K 8/22 424/62 |
| 2012/0315236 A1 | 12/2012 | Goutsis et al. | |
| 2014/0271750 A1* | 9/2014 | Schulze zur Wiesche | A61Q 5/12 424/401 |

FOREIGN PATENT DOCUMENTS

EP  2191812 A1  6/2010

OTHER PUBLICATIONS

PCT International Search Report (PCT/EP2014/051681) dated Jun. 5, 2014.

* cited by examiner

*Primary Examiner* — Jyothsna Venkat
(74) *Attorney, Agent, or Firm* — P. Scott Smith

(57) ABSTRACT

The present invention relates, in a first embodiment, to agents for lightening keratinic fibers, containing at least two separately packaged preparations (A) and (B), and optionally a further preparation (C) packaged separately from (A) and (B), which are mixed immediately prior to application to form an application mixture. Preparation (A) includes at least one persulfate, at least one acrylate polymer, and carboxymethylcellulose, and preparation (B) is flowable and includes at least one oxidizing agent. Preparation (A) includes, based on its weight, a1) 0 to 3% by weight of keratin hydrolysate(s) and/or a2) 0 to 5% by weight of silicone oil(s), with the condition that preparation (A) includes, based on its weight, 0.1 to 6% by weight of compound(s) from the groups a1) and a2).

11 Claims, No Drawings

POLYMER-CONTAINING TRANSPARENT BLEACHING COMPOSITIONS WITH PROTEINS AND/OR SILICONE OILS

FIELD OF THE INVENTION

The present invention generally relates to agents for oxidatively changing color in the field of cosmetics, which are particularly suited for lightening keratinic fibers, in particular human hair.

BACKGROUND OF THE INVENTION

The oxidizing agents contained in bleaching agents are able to lighten the hair fiber by oxidative destruction of the hair's own dye, melanin. For a moderate bleaching effect, use of hydrogen peroxide alone, optionally using ammonia or other alkalizing agents, as oxidizing agent is sufficient; for achieving a more intense bleaching effect, a mixture of hydrogen peroxide and peroxydisulfate salts is customarily used.

For stability reasons, commercially available bleaching agents are usually provided in two separately packaged preparations which are mixed immediately prior to application to form a final use preparation. Commercially available bleaching agents are customarily composed of a liquid oxidizing agent preparation and a powder which includes solid oxidizing agents. Products having further components are likewise commercially available.

WO 2005/067874 A1 describes bleaching agents which contain a mixture of an oxidizing agent, at least one stabilizer, at least one polymer thickener composed of synthetic polymers and alkali magnesium silicates, and water or an aqueous solvent. "Transparency" and "thickened consistency" are stated as desirable properties of the agent according to this invention.

DE 10 2010 042 252 A1 discloses agents for lightening keratinic fibers, containing at least two separately packaged preparations (A) and (B) and optionally a further preparation (C) packaged separately from (A) and (B), which are mixed immediately prior to application to form an application mixture, wherein preparations (A) contain at least one persulfate and preparations (B) are flowable and contain at least one oxidizing agent, and preparations (B) and/or preparations (C) additionally contain at least one natural polymer.

The oxidative treatment of keratinic fibers does not result in the desired lightening result; it stresses the fibers, and in the worst case scenario may damage the fiber structure. To minimize these negative effects, care substances which have reparative and conditioning effects are used in conventional, nontransparent bleaching agents not according to the invention. However, in transparent bleaching agents, many of the care substances commonly used result in loss or marked impairment of the transparency, which counteracts the benefit of applying these agents. Other care substances weaken the bleaching power, so that their use is contraindicated.

The object of the present invention is to improve the properties of bleaching agents with regard to their care properties without impairing their performance.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

Agent for lightening keratinic fibers, containing at least two separately packaged preparations (A) and (B) and optionally a further preparation (C) packaged separately from (A) and (B), which are mixed immediately prior to application to form a use preparation, wherein preparation (A) includes at least one persulfate, at least one acrylate polymer, and carboxymethylcellulose and preparation (B) is flowable and includes at least one oxidizing agent, characterized in that preparation (A) includes, based on its weight, 0 to 3% by weight of keratin hydrolysate(s) and/or 0 to 5% by weight of silicone oil(s), with the condition that preparation (A) includes, based on its weight, 0.1 to 6% by weight of compound(s) from the groups a1) and a2).

Method for changing the color of keratinic fibers, in which at least two separately packaged preparations (A) and (B), of which preparation (A) includes at least one persulfate, at least one acrylate polymer, and carboxymethylcellulose, and preparation (B) includes at least one oxidizing agent, are mixed to form an application mixture, which is applied to the fibers and rinsed off after an exposure period, characterized in that preparation (A) includes, based on its weight, 0 to 3% by weight of keratin hydrolysate(s) and/or 0 to 5% by weight of silicone oil(s), with the condition that preparation (A) includes, based on its weight, 0.1 to 6% by weight of compound(s) from the groups a1) and a2).

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has been shown that certain thickeners may be easily incorporated into bleaching powder, and when mixed with oxidizing agent preparations result in a flowable preparation which allows good homogenization of the two components to form a final mixed application mixture. In this particular matrix, certain proteins in combination with or without silicone oil result in long-lasting care effects, and the bleaching power is also intensified. In a first embodiment, the subject matter of the present invention relates to agents for lightening keratinic fibers, containing at least two separately packaged preparations (A) and (B) and optionally a preparation (C) which is packaged separately from (A) and (B), which are mixed immediately prior to application to form an application mixture, wherein i. preparation (A) includes at least one persulfate, at least one acrylate polymer, and carboxymethylcellulose and
  ii. preparation (B) is flowable and includes at least one oxidizing agent, and preparation (A) includes, based on its weight,
  a1) 0 to 3% by weight of keratin hydrolysate(s) and/or
  a2) 0 to 5% by weight of silicone oil(s),
with the condition that preparation (A) includes, based on its weight, 0.1 to 6% by weight of compound(s) from the groups a1) and a2).

Keratinic fibers or keratin fibers are understood to mean fur, wool, feathers, and in particular human hair. Although the agents according to the invention are primarily suited for lightening keratin fibers, use in other fields is also possible in principle.

The preparations (A) are preferably powdered. Powders from solid components having different particle sizes may be used. Typically, however, it may be preferable for the powders to have the most homogeneous particle size possible, in particular to facilitate uniform dispersion or dissolution of the powders in the preparations (B).

The preparations (A) may contain the active substances in a solid cosmetic carrier. A solid cosmetic carrier may contain salts of silicic acid, in particular salts of the silicates and metasilicates, with ammonium, alkali metals, and alkaline earth metals. In particular metasilicates, which according to formula $(SiO_2)_n(M_2O)_m$, where M stands for an ammonium ion, an alkali metal, or one-half stoichiometric equivalent of an alkaline earth metal, are characterized by an n:m ratio of ≤1 and understood as chain-type polymeric structures of the $[SiO_3]^{2-}$ anion, may preferably be used. Sodium metasilicate of formula $[Na_2SiO_3]_\infty$ is particularly preferred. Also preferred according to the invention are silicates which are formed from a silicate of formula $(SiO_2)_n(Na_2O)_m(K_2O)_p$, where n stands for a positive rational number and m and p independently stand for a positive rational number or for 0, with the condition that at least one of the parameters m or p is different from 0, and the ratio of n to the sum of m and p is between 2:1 and 4:1.

In addition, the solid cosmetic carriers may contain so-called anti-caking agents which are intended to prevent clumping or caking of the powder components. Water-insoluble, water-repellent, or moisture-adsorbing powders of diatomaceous earth, pyrogenic silicic acids, calcium phosphate, calcium silicates, aluminum oxide, magnesium oxide, magnesium carbonate, zinc oxide, stearates, fatty amines, and the like are preferred as such anti-caking agents. Lastly, the solid cosmetic carriers may additionally contain a dust control agent which prevents the formation of dust from the powdered components. Inert oils in particular may be used for this purpose. The solid cosmetic carriers preferably contain ester oils or mineral oils, preferably hydrocarbon oils such as liquid paraffin oil, as dust control agent.

As the first essential ingredient, preparation (A) includes at least one persulfate.

Persulfates which are suitable according to the invention are inorganic peroxo compounds. These are preferably selected from ammonium peroxodisulfate, alkali metal peroxodisulfates, ammonium peroxomonosulfate, alkali metal peroxomonosulfates, alkali metal peroxodiphosphates, and/or alkaline earth metal peroxides.

Ammonium peroxodisulfate and/or alkali metal peroxodisulfates is/are particularly preferred.

In one preferred embodiment of the present invention, preparation (A) includes as persulfate at least one peroxodisulfate salt, in particular selected from ammonium peroxodisulfate and/or potassium peroxodisulfate and/or sodium peroxodisulfate.

Furthermore, in the studies leading to the present invention it has proven to be particularly preferred when the preparations (A) contain at least two different peroxodisulfates. Preferred peroxodisulfate salts are combinations of ammonium peroxodisulfate with potassium peroxodisulfate and/or sodium peroxodisulfate.

The preparations (A) preferably contain persulfate salts in a quantity of 0.1 to 80% by weight, preferably 2 to 50% by weight, particularly preferably 3 to 30% by weight, very particular preferably 5 to 15% by weight, and explicitly 5, 6, 7, 8, 9, 10, 11, 12, 13, 14, or 15% by weight, in each case based on the total weight of the agent.

As further essential ingredients, preparation (A) includes at least one acrylate polymer and carboxymethylcellulose.

Within the meaning of the present patent application, acrylate polymers are polymers which contain monomer units of acrylic acid and/or methacrylic acid and their respective derivatives. For example, homopolymers such as polyacrylic acid, polymethacrylic acid, and their respective salts and/or esters may be used.

Such homopolymers contain solely structural units of formula (I)

in which R1 stands for —H or —$CH_3$, and R2 stands for —H or —$CH_3$ or —$CH_2CH_3$ or —$CH_2CH_2CH_3$ or —$CH(CH_3)_2$. When R1 stands for —H, the underlying monomers of formula (I) are acrylic acid or acrylic acid ester, and when R1=—$CH_3$, the underlying monomers of formula (I) are methacrylic acid or methacrylic acid ester.

R2 may also completely or partially stand for $Na^+$, $K^+$, $NH_4^+$, or the nth part of a cation having a charge n; in this case, the homopolymers are (partially) neutralized polyacids. However, copolymers having further monomers are also usable according to the invention. Examples of preferred acrylate copolymers are polyacrylic acid and/or copolymers of methacrylic acid with acrylamidopropanesulfonic acid, and/or copolymers of acrylic acid with methacrylic acid and acrylic acid esters, and/or copolymers of acrylic acid with methacrylic acid, acrylic acid esters, and methacrylic acid esters, and/or copolymers of acrylic acid esters with methacrylic acid.

Na-carboxymethylcellulose is the sodium salt of the glycolic acid ether of cellulose. Na-carboxymethylcellulose is commercially produced by reacting alkali cellulose with monochloroacetic acid or the sodium salt thereof. The degree of substitution indicates how many of the radicals R in the above formula stand for hydrogen atoms or —$CH_2$—COONa groups. A degree of substitution of 1 means that one of the six radicals R per repeating formula unit stands for a —$CH_2$—COONa group, while the remaining five radicals are —H.

It is preferred according to the invention to use the Na—CMC in fairly narrow quantity ranges. Quantities of 0.25 to 4.0% by weight, preferably 0.5 to 3.0% by weight, particularly preferably 0.75 to 2.5% by weight, and in particular 1.0 to 1.75% by weight, based on the weight of preparation (A), are particularly preferred.

Regardless of the quantity of Na—CMC used, carboxymethylcelluloses which have a degree of substitution of 0.75 to 0.85 are preferred.

According to the invention, preparation (A) includes, based on its weight,
 a1) 0 to 3% by weight of keratin hydrolysate(s) and/or
 b1) 0 to 5% by weight of silicone oil(s),
with the condition that preparation (A) includes, based on its weight, 0.1 to 6% by weight of compound(s) from the groups a1) and a2).

Agents according to the invention may accordingly contain solely keratin hydrolysate(s) in preparation (A), in that case in quantities of 0.1 to 3% by weight, or solely silicone oil(s), in that case in quantities of 0.1 to 5% by weight, or keratin hydrolysate(s) as well as silicone oil(s), in that case in total quantities of the two ingredients of 0.1 to 6% by weight, in each case based on the weight of preparation (A). Agents preferred according to the invention are characterized in that preparation (A) includes 0.01 to 1% by weight, preferably 0.05 to 0.75% by weight, more preferably 0.1 to 0.5% by weight, particularly preferably 0.15 to 0.4% by weight, and in particular 0.2 to 0.3% by weight, of hydrolysate(s) having molar masses of 400 to 1200 Dalton, obtained from the cortex and/or the cuticle of keratinic fibers.

Further agents which are preferred according to the invention are characterized in that preparation (A) includes 0.01 to 5% by weight, preferably 0.05 to 4% by weight, more preferably 0.1 to 2.5% by weight, particularly preferably 0.25 to 2% by weight, and in particular 0.5 to 1.5% by weight, of silicone oil(s) from the group of compounds having the INCI name Dimethicone.

Dimethicones may be both linear and branched, as well as cyclic or cyclic and branched. Linear dimethicones may be represented by the following structural formula (Si1):

Branched dimethicones may be represented by structural formula (Si1.1):

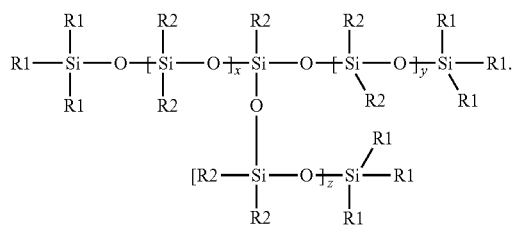

The radicals $R^1$ and $R^2$ each independently stand for hydrogen, a methyl radical, a C2 to C30 linear, saturated, or unsaturated hydrocarbon radical, a phenyl radical, and/or an aryl radical. Non-limiting examples of the radicals represented by $R^1$ and $R^2$ include alkyl radicals such as methyl, ethyl, propyl, isopropyl, butyl, isobutyl, pentyl, isopentyl, neopentyl, amyl, isoamyl, hexyl, isohexyl, and the like; alkenyl radicals such as vinyl, halovinyl, alkyl vinyl, allyl, haloallyl, alkyl allyl; cycloalkyl radicals such as cyclobutyl, cyclopentyl, cyclohexyl, and the like; phenyl radicals, benzyl radicals, halogenated hydrocarbon radicals such as 3-chloropropyl, 4-bromobutyl, 3,3,3-trifluoropropyl, chlorocyclohexyl, bromophenyl, chlorophenyl, and the like; and sulfur-containing radicals such as mercaptoethyl, mercaptopropyl, mercaptohexyl, mercaptophenyl, and the like; $R^1$ and $R^2$ are preferably an alkyl radical which includes 1 to approximately 6 carbon atoms, and $R^1$ and $R^2$ are most preferably methyl. Examples of $R^1$ include methylene, ethylene, propylene, hexamethylene, decamethylene, —CH$_2$CH(CH$_3$)CH$_2$—, phenylene, naphthylene, —CH$_2$CH$_2$SCH$_2$CH$_2$—, —CH$_2$CH$_2$OCH$_2$—, —OCH$_2$CH$_2$—, —OCH$_2$CH$_2$CH$_2$—, —CH$_2$CH(CH$_3$)C(O)OCH$_2$—, —(CH$_2$)$_3$CC(O)OCH$_2$CH$_2$—, —C$_6$H$_4$C$_6$H$_4$—, —C$_6$H$_4$CH$_2$C$_6$H$_4$—; and —(CH$_2$)$_3$C(O)SCH$_2$CH$_2$—. Methyl, phenyl, and C2 to C22 alkyl radicals are preferred as $R^1$ and $R^2$. Lauryl, stearyl, and behenyl radicals are very particularly preferred for the C2 to C22 alkyl radicals. The numbers x, y, and z are integers, and independently have a value from 0 to 50,000. The molar weights of the dimethicones are between 1000 D and 10,000,000 D. The viscosities are between 100 and 10,000,000 cPs, measured at 25° C. using a glass capillary viscometer according to Dow Corning Corporate Test Method CTM 0004, Jul. 20, 1970. Preferred viscosities are between 1000 and 5,000,000 cPs, and very particularly preferred viscosities are between 10,000 and 3,000,000 cPs. The most preferred range is between 50,000 and 2,000,000 cPs. Viscosities around the range of approximately 60,000 cPs are extremely preferred. The word "approximately" defines a deviation, customary to those skilled in the art in commercially produced products, from the stated value which follows the word "approximately." Reference is made here to the product "Dow Corning 200 with 60,000 cSt" as an example.

The teaching according to the invention naturally also encompasses that the dimethicones may already be present as an emulsion.

When the dimethicones are used as an emulsion, according to the invention the droplet size of the emulsified particles is 0.01 to 10,000 μm, preferably 0.01 to 100 μm, very particularly preferably 0.01 to 20 μm, and most preferably 0.01 to 10 μm. The particle size is determined according to the light scattering method.

Particularly preferred agents according to the invention are characterized in that preparation (A) includes 0.01 to 5% by weight, preferably 0.05 to 4% by weight, more preferably 0.1 to 2.5% by weight, particularly preferably 0.25 to 2% by weight, and in particular 0.5 to 1.5% by weight, of at least one silicone of formula (Si-I)

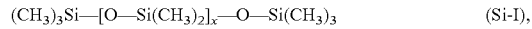

in which x stands for a number from 0 to 100, preferably from 0 to 50, more preferably from 0 to 20, and in particular from 0 to 10.

Further agents which are preferred according to the invention are characterized in that preparation (A) includes 0.01 to 5% by weight, preferably 0.05 to 4% by weight, more preferably 0.1 to 2.5% by weight, particularly preferably 0.25 to 2% by weight, and in particular 0.5 to 1.5% by weight, of silicone oil(s) from the group of compounds having the INCI name Amodimethicone, wherein compounds having the INCI names Silicone Quaternium-1, Silicone Quaternium-2, Silicone Quaternium-3, Silicone Quaternium-4, Silicone Quaternium-5, Silicone Quaternium-6, Silicone Quaternium-7, Silicone Quaternium-8, Silicone Quaternium-9, Silicone Quaternium-10, Silicone Quaternium-11, Silicone Quaternium-12, Silicone Quaternium-15, Silicone Quaternium-16, Silicone Quaternium-17, Silicone Quaternium-18, Silicone Quaternium-20, Silicone Quaternium-21, or Silicone Quaternium-22 are preferred.

It has been shown that in particular 4-morpholinomethyl-substituted silicones result in particularly good care results without impairing the transparency of the agents. Particularly preferred agents according to the invention are characterized in that preparation (A) includes 0.01 to 5% by weight, preferably 0.05 to 4% by weight, more preferably 0.1 to 2.5% by weight, particularly preferably 0.25 to 2% by weight, and in particular 0.5 to 1.5% by weight, of silicone oil(s) of formula (I)

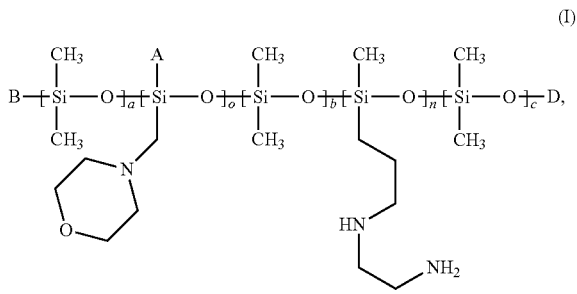

in which

A stands for a structural unit (I), (II), or (III) bound via an —O—

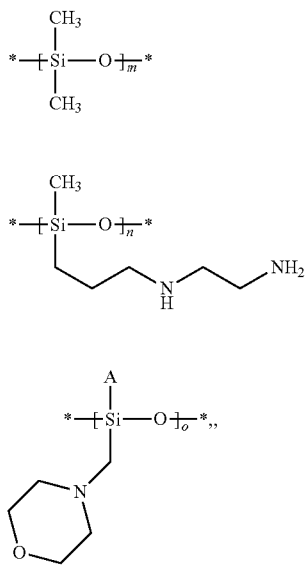

or an oligomeric or polymeric radical, bound via an —O—, containing structural units of formulas (I), (II), or (III), or one-half of a connecting O atom to a structural unit (III), or for —OH,

* stands for a bond to one of the structural units (I), (II), or (III), or for an end group B (Si-bound) or D (O-bound), B stands for an —OH, —O—Si(CH$_3$)$_3$, —O—Si(CH$_3$)$_2$OH, —O—Si(CH$_3$)$_2$OCH$_3$ group, D stands for an —H, —Si(CH$_3$)$_3$, —Si(CH$_3$)$_2$OH, —Si(CH$_3$)$_2$OCH$_3$ group, a, b, and c stand for integers between 0 and 1000, with the condition that a+b+c>0, m, n, and o stand for integers between 1 and 1000.

Such preferred agents contain in preparation (A) 0.01 to 5% by weight, preferably 0.05 to 4% by weight, more preferably 0.1 to 2.5% by weight, particularly preferably 0.25 to 2% by weight, and in particular 0.5 to 1.5% by weight, of at least one 4-morpholinomethyl-substituted silicone of structural formula (I). This clarifies that the siloxane groups n and o do not necessarily have to be bound directly to an end group B or D. Instead, in preferred formulas (I), a>0 or b>0 applies, and in particularly preferred formulas (I), a>0 and b>0 applies; i.e., the terminal group B or D is preferably bound to a dimethylsiloxy group. In addition, in formula (I) the siloxane units a, b, c, n, and o are preferably statistically distributed.

The silicones used according to the invention and illustrated by formula (I) may be trimethylsilyl-terminated on both sides (D=—Si(CH$_3$)$_3$, B=—O—Si(CH$_3$)$_3$), but may also be dimethylsilylhydroxy- or dimethylsilylmethoxy-terminated on one or both sides. Silicones which are particularly preferably used within the scope of the present invention have at least one terminal dimethylsilylhydroxy group, i.e., are selected from silicones in which B=—O—Si(CH$_3$)$_2$OH and D=—Si(CH$_3$)$_3$
B=—O—Si(CH$_3$)$_2$OH and D=—Si(CH$_3$)$_2$OH
B=—O—Si(CH$_3$)$_2$OH and D=—Si(CH$_3$)$_2$OCH$_3$
B=—O—Si(CH$_3$)$_3$ and D=—Si(CH$_3$)$_2$OH
B=—O—Si(CH$_3$)$_2$OCH$_3$ and D=—SiCH$_3$)$_2$OH.

These silicones result in enormous improvements in the properties of hair treated with the agents according to the invention, and in particular result in a significant reduction in the contact angle.

The structural units of formulas (I), (II), and (III) may be statistically distributed in the molecule; however, the silicones used according to the invention may also be block copolymers composed of blocks of the individual structural units, and the blocks in turn may be present in a statistical distribution. The "*" at the free valences of the structural units (I), (II), or (III) stands for a bond to one of the structural units (I), (II), or (III) or for an end group B (Si-bound) or D (O-bound). In formula (I), the radical A may stand for a structural unit (I), (II), or (III) bound via an —O— or an oligomeric or polymeric radical, bound via an —O—, containing structural units of formulas (I), (II), or (III) or one-half of a connecting O atom to a structural unit (III), or for —OH.

Thus, formula (I) is refined to form one of formulas (Ia), (Ib), (Ic), (Id), (Ie), or (If):

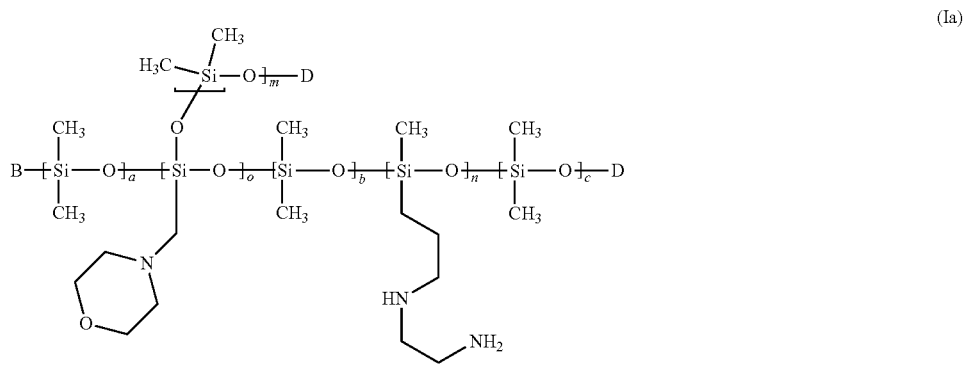

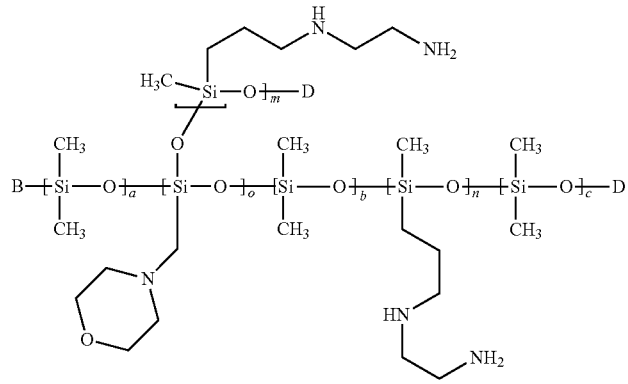
(Ib)
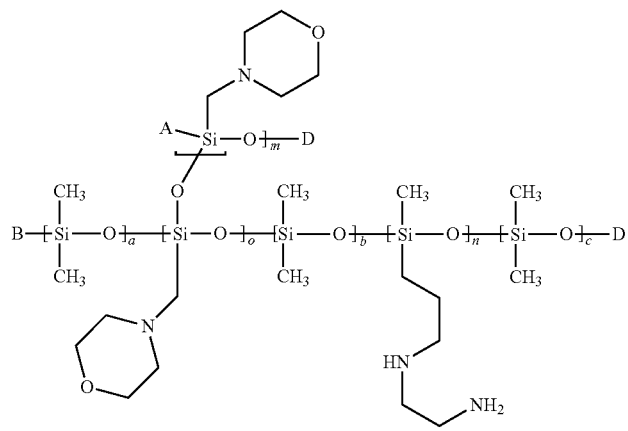
(Ic)
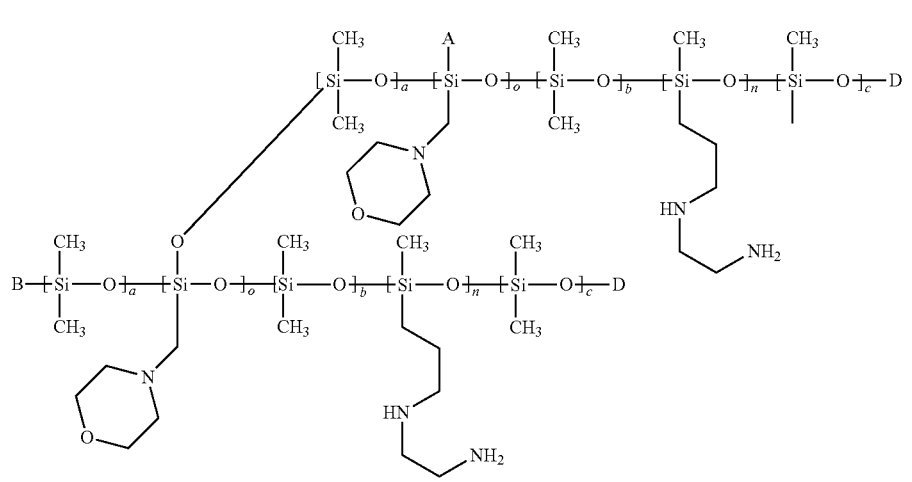
(Id)

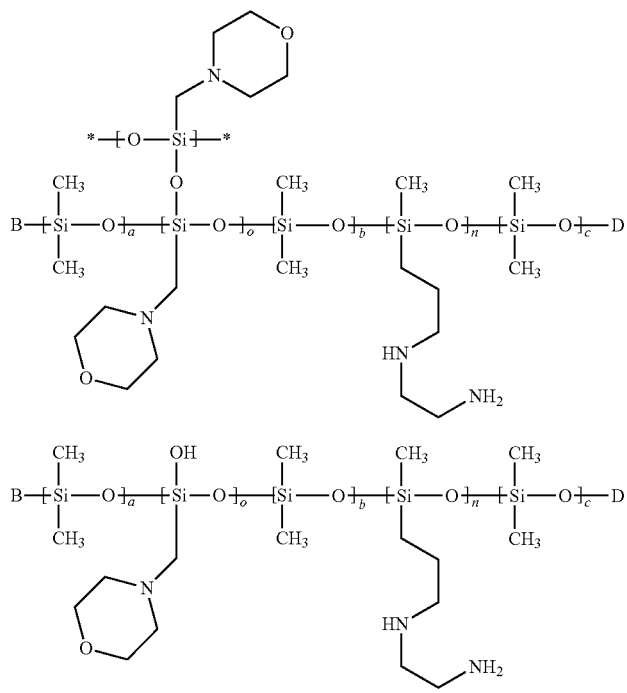

In structural unit (III), radical A may stand for
a structural unit (I), (II), or (III) bound via an —O— or
an oligomeric or polymeric radical, bound via an —O—,
  containing structural units of formulas (I), (II), or (III)
  or
one-half of a connecting O atom to a structural unit (III),
  or for —OH.

In the first-mentioned case, structural unit (III) becomes one of structural units (IIIa), (IIIb), or (IIIc):

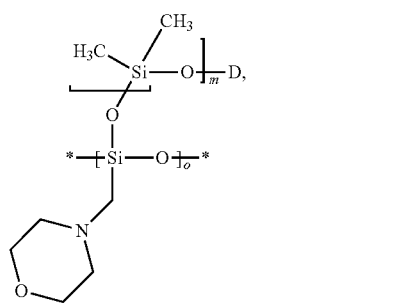

(IIIa)

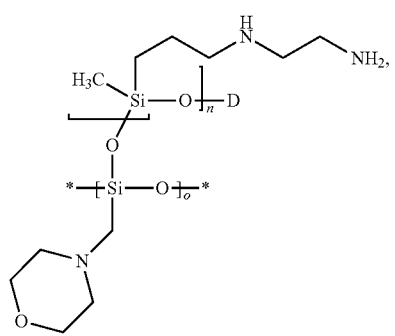

(IIIb)

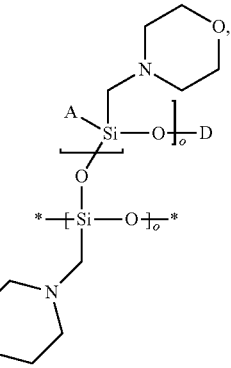

(IIIc)

where m=n=o=1, and A and D are defined as above.

In the second case, in the above-mentioned formulas (IIIa), (IIIb), and (IIIc) the Indices m, n, and o may stand for integers between 2 and 1000. However, the second case also covers oligomeric or polymeric radicals containing at least two different structural units of formulas (I), (II), or (III), as illustrated in formula (IIId):

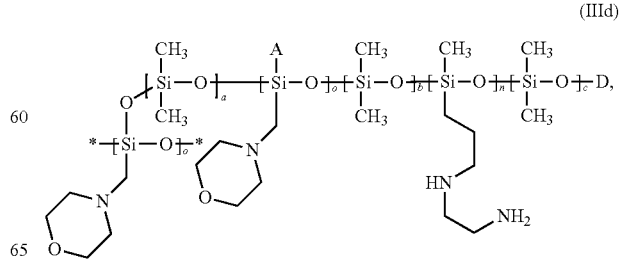

(IIId)

in which a, b, and c for stand for integers between 0 and 1000, with the condition that a+b+c>0, and n and o stand for integers between 1 and 1000.

In the third case, A stands for one-half of a connecting O atom to a structural unit (III) in structural unit (IIIe), or for —OH (illustrated in structural unit (IIIf)):

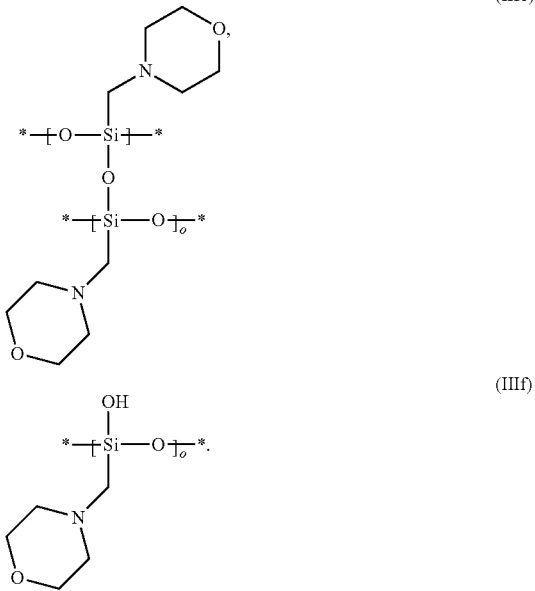

(IIIe)

(IIIf)

Structural unit (III) or the siloxane units o in formula (I) may form nested or partial cage structures via group A, when A stands for one-half of a connecting O atom to a structural unit (III). Hair treatment agents according to the invention which contain silicones having corresponding 4-morpholinomethyl-substituted silsesquioxane substructures are preferred according to the invention, since these silicones result in enormously improved compatibility and drastically reduced contact angles.

Accordingly, agents preferred according to the invention are characterized in that composition (A) includes at least one 4-morpholinomethyl-substituted silicone which has structural units of formula (II)

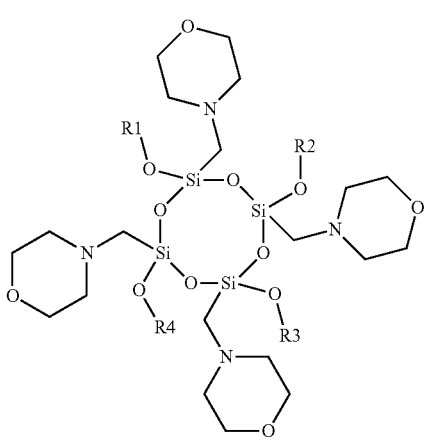

(II)

in which
R1, R2, R3, and R4 independently stand for —H, —CH$_3$, a D group, a structural unit (I), (II), or (III), or an oligomeric or polymeric radical containing structural units of formulas (I), (II), or (III), or
two of the radicals R1, R2, R3, and R4 stand for an —Si(R6)(R5)- structural unit, where
R5=—CH$_3$ or a structural unit of formula (I) or (II) or (III) or an oligomeric or polymeric radical containing structural units of formulas (I), (II), or (III)
R6=—OH, —CH$_3$, or a structural unit of formula (I) or (II) or (III) or an oligomeric or polymeric radical containing structural units of formulas (I), (II), or (III).

In preferred silicones of formula (II), at least one of the radicals R1, R2, R3, or R4 stands for an oligomeric or polymeric radical containing structural units of formulas (I), (II), or (III).

In further preferred silicones of formula (II), at least one of the radicals R1, R2, R3, or R4 stands for an oligomeric or polymeric radical containing structural units of formulas (I) and (II).

In even further preferred silicones of formula (II), at least one of the radicals R1, R2, R3, or R4 stands for an oligomeric or polymeric radical containing structural units of formulas (I) and (II) and (III).

At least one of the radicals R1, R2, R3, or R4 preferably stands for a —[—Si(CH$_3$)$_2$—O]$_m$ group, i.e., an oligomer or polymer of structural unit (I). In addition, structural unit (II) or an oligomer or polymer thereof is preferably never bound alone, but instead, is always bound in a statistical distribution with further structural units of formula (I) as one of the radicals R1, R2, R3, or R4 in the molecule.

Regardless of which particular 4-morpholinomethyl-substituted silicone is used in preparation (A), agents according to the invention are preferred which contain in preparation (A) a 4-morpholinomethyl-substituted silicone in which more than 50 mol-% of the structural units are dimethylsiloxy units, i.e., in which structural unit (I) constitutes at least one-half of all structural units of the silicone used.

In other words, silicones are preferred in which m>(n+o) or (a+b+c)>(n+o) applies.

Even further preferred agents contain in preparation (A) a 4-morpholinomethyl-substituted silicone in which more than 90 mol-% of the structural units are dimethylsiloxy units, i.e., in which structural unit (I) constitutes at least nine-tenths of all structural units of the silicone used.

In other words, silicones are preferred in which m>10 (n+o) or (a+b+c)>10 (n+o) applies. Even further preferred cosmetic agents contain a 4-morpholinomethyl-substituted silicone in which more than 98 mol-% of the structural units are dimethylsiloxy units, i.e., in which structural unit (I) constitutes at least 98 percent of all structural units of the silicone used.

In other words, silicones are preferred in which m>50 (n+o) or (a+b+c)>50 (n+o) applies. Even further preferred cosmetic agents contain a 4-morpholinomethyl-substituted silicone in which more than 98.5 mol-% of the structural units are dimethylsiloxy units, i.e., in which structural unit (I) constitutes at least 98.5% of all structural units of the silicone used.

In other words, silicones are preferred in which m>75 (n+o) or (a+b+c)>75 (n+o) applies. Even further preferred cosmetic agents contain a 4-morpholinomethyl-substituted silicone in which more than 99 mol-% of the structural units are dimethylsiloxy units, i.e., in which structural unit (I) constitutes at least ninety-nine hundredths of all structural units of the silicone used.

In other words, silicones are preferred in which m>100 (n+o) or (a+b+c)>100 (n+o) applies. In summary, agents which are preferred according to the invention are characterized in that they contain at least one 4-morpholinomethyl-substituted silicone in preparation (A), in which
m>(n+o) or (a+b+c)>(n+o),
preferably m>10 (n+o) or (a+b+c)>10 (n+o),
particularly preferably m>50 (n+o) or (a+b+c)>50 (n+o),
more preferably m>75 (n+o) or (a+b+c)>75 (n+o), and
n particular m>100 (n+o) or (a+b+c)>100 (n+o) applies.

It has been shown that the effect of the silicones used according to the invention may be even further increased when certain nonionic components are also used in the agents according to the invention. In addition, these nonionic components have positive effects on the storage stability of the agents according to the invention. Nonionic components which are particularly suitable here are ethoxylates of decanol, undecanol, dodecanol, tridecanol, etc. Ethoxylated tridecanols which are particularly preferably incorporated into the agents according to the invention have proven to be particularly suitable. Cosmetic compositions which are particularly preferred according to the invention contain, based on their weight, 0.00001 to 5% by weight, preferably 0.0001 to 3.5% by weight, particularly preferably 0.001 to 2% by weight, more preferably 0.01 to 1% by weight, and in particular 0.1 to 0.5% by weight, of branched ethoxylated tridecanol (INCI name: Trideceth-5) or α-isotridecyl-ω-hydroxypolyglycol ether (INCI name: Trideceth-10) or the mixtures thereof.

Morpholinomethyl-substituted silicone(s) which is/are preferred according to the invention has/have hydroxy as well as alkoxy groups. Agents which are particularly preferred according to the invention contain in preparation (A) hydroxy-terminated 4-morpholinomethyl-substituted silicone(s) in which the mole ratio of hydroxy to alkoxy is in the range of 0.2:1 to 0.4:1, preferably in the range of 1:0.8 to 1:1.1. The average molecular weight of the silicone is preferably 2,000 to 200,000 Dalton, even more preferably 5,000 to 100,000 Dalton, in particular 10,000 to 50,000 Dalton. Cosmetic compositions in which the weight average molar mass of the 4-morpholinomethyl-substituted silicone of formula (I) contained therein is in the range of 2,000 to 1,000,000 $gmol^{-1}$, preferably in the range of 5,000 to 200,000 $gmol^{-1}$, are preferred.

The average molecular weights of amino-substituted silicones are measurable, for example, by gel permeation chromatography (GPC) at room temperature in polystyrene. μ-Styragel columns may be selected as columns, THF may be selected as eluent, and 1 mL/min may be selected as the flow rate. The detection is preferably carried out by refractometry, using a UV meter.

According to the invention, preparation (B) and/or preparation (C) also contain(s) at least one natural polymer (see below). Preparation (A) is preferably free of xanthan, since it has been shown that this improves the lightening power.

Agents preferred according to the invention are characterized in that preparation (A) is free of xanthan and preferably includes, based on its weight, 5 to 60% by weight, 10 to 55% by weight, particularly preferably 15 to 50% by weight, and in particular 20 to 45% by weight, of at least one persulfate selected from ammonium peroxodisulfate and/or potassium peroxodisulfate and/or sodium peroxodisulfate.

The first subject matter of the invention comprises agents for lightening keratinic fibers, containing at least two separately packaged preparations (A) and (B) and optionally a further preparation (C) which is packaged separately from (A) and (B). Preparation (B) and optionally preparation (C) contain the active substances in a flowable cosmetic carrier. The basis of the flowable cosmetic carrier is preferably aqueous or aqueous-alcoholic. For purposes of hair bleaching, such carriers are, for example, transparent gels or also surfactant-containing foaming solutions, for example shampoos, foam aerosols, or other preparations which are suitable for application to the hair. Within the meaning of the invention, a preferred flowable carrier includes at least 40% by weight, in particular at least 50% by weight, of water. Within the meaning of the present invention, aqueous-alcoholic carriers are understood to mean water-containing compositions which contain 3 to 70% by weight of a $C_1$-$C_4$ alcohol, in particular ethanol or isopropanol. The agents according to the invention may additionally contain further organic solvents, for example methoxybutanol, ethyl diglycol, 1,2-propylene glycol, n-propanol, n-butanol, n-butylene glycol, glycerin, diethylene glycol monoethyl ether, and diethylene glycol mono-n-butyl ether. All water-soluble organic solvents are preferred.

As an essential ingredient, preparations (B) and/or preparations (C) of the bleaching agent according to the invention contain at least one oxidizing agent.

In one particular embodiment, preparations (B) according to the invention contain hydrogen peroxide as oxidizing agent.

The concentration of a hydrogen peroxide solution in oxidizing agent preparation (B) is determined on the one hand by regulatory requirements, and on the other hand by the desired effect. The preparations (B) preferably contain, based on their weight, hydrogen peroxide in quantities of 0.5 to 30% by weight, preferably 1 to 20% by weight, particularly preferably 5 to 15% by weight, very particular preferably 6 to 12% by weight, and explicitly 6, 7, 8, 9, 10, 11, or 12% by weight.

Ready-to-use agents which are preferred according to the invention are characterized in that they contain, based on the total weight of the ready-to-use agent, 0.01 to 12% by weight, preferably 0.1 to 10% by weight, particularly preferably 1 to 8% by weight, of hydrogen peroxide.

Ready-to-use agents which are preferred according to the invention are characterized in that they contain, based on the total weight of the ready-to-use agent, 0.01 to 12% by weight, preferably 0.1 to 10% by weight, particularly preferably 1 to 8% by weight, of hydrogen peroxide.

For stabilizing the hydrogen peroxide, the pH of preparation (B) may preferably be set to pH 3 to 5, particularly preferably to pH 3.5 to 4.5, and very particularly preferably to pH 3.8 to 4.2.

Preparation (B) (and/or preparation (C)) may also contain a natural polymer for regulating the viscosity. When the agent for lightening keratinic fibers includes exactly two separately packaged preparations (A) and (B) which are mixed immediately prior to application to form an application mixture, preparation (B) includes at least one natural polymer according to this embodiment of the invention.

When the agent for lightening keratinic fibers includes at least three separately packaged preparations (A), (B), and (C) which are mixed immediately prior to application to form an application mixture, preparation (B) and/or preparation (C) may contain at least one natural polymer.

For example, cellulose derivatives which are used as thickeners may be used as natural polymer. Examples are agar-agar, carrageenan, alginates, xanthan gum, karaya gum, gum ghatti, tragacanth, scleroglucan gums, or gum arabic, alginates, pectins, polyoses, guar gums, locust bean gum, linseed gums, dextrans, pectins, starch fractions, and derivatives such as amylose, amylopectin, and dextrins, gelatins, and casein, and cellulose derivatives such as methylcellulose, carboxyalkylcelluloses such as carboxymethylcellulose, and hydroxyalkylcelluloses such as hydroxyethylcellulose.

Natural polymers from the named substance classes are commercially available, and are marketed, for example, under the trade names Deuteron®-XG (anionic heteropolysaccharide based on β-D-glucose, D-mannose, D-glucuronic acid, Schoener GmbH), Deuteron®-XN (nonionogenic polysaccharide, Schoener GmbH), Protanal RF 6650 Alginate (sodium alginate, FMC Biopolymer), Cekol (cellulose gum, Kelco), Kelzan (xanthan biopolymer, Kelco), xanthan FN (xanthan biopolymer, Jungbunzlauer), Keltrol, for example Keltrol CG-T (xanthan biopolymer, Kelco), or Keltrol CG-SFT (xanthan biopolymer, Kelco).

In one preferred embodiment of the invention, preparation (B) and/or preparation optionally (C) contain(s) xanthan.

Xanthans which result in transparent preparations after swelling are preferred according to the invention. Use of the xanthan biopolymer, which is marketed by Kelco under the trade name Keltrol CG-SFT, is particularly preferred.

In one preferred embodiment, preparation (B) includes, based on its weight, xanthan in quantities of 0.1 to 10% by weight, preferably 0.5 to 6% by weight, particularly preferably 0.7 to 5% by weight, very particularly preferably 1 to 4% by weight, explicitly 1, 2, 3, or 4% by weight, when the agent for lightening keratinic fibers includes exactly two separately packaged preparations (A) and (B) which are mixed immediately prior to application to form an application mixture. The final mixed use preparations preferably contain, based on their weight, xanthan in quantities of 0.6 to 5% by weight, particularly preferably 1.0 to 3.5% by weight, very particularly preferably 1.5 to 2.5% by weight, and explicitly 1.5; 1.6; 1.7; 1.8; 1.9; 2.0; 2.1; 2.2; 2.3; 2.4; or 2.5% by weight.

When the agent for lightening keratinic fibers includes at least three separately packaged preparations (A), (B), and (C) which are mixed immediately prior to application to form an application mixture, preparation (B) and/or preparation (C) may contain xanthan. When the agent for lightening keratinic fibers includes at least three separately packaged preparations (A), (B), and (C) which are mixed immediately prior to application to form an application mixture, preparations are preferred in which preparation (C) includes xanthan. Preparations in which preparation (C) includes xanthan and preparation (B) is free of xanthan are particularly preferred.

Regardless of whether preparation (B) and/or preparation (C) contain(s) xanthan, final mixed use preparations are preferred which contain, based on the weight of the final use preparation, xanthan in quantities of 0.6 to 5% by weight, particularly preferably 1.0 to 3.5% by weight, very particularly preferably 1.5 to 2.5% by weight, explicitly 1.5; 1.6; 1.7; 1.8; 1.9; 2.0; 2.1; 2.2; 2.3; 2.4; or 2.5% by weight.

Agents which are particularly preferred according to the invention are characterized in that preparation (B) includes, based on its weight, 0.1 to 10% by weight, preferably 0.25 to 7.5% by weight, more preferably 0.5 to 5% by weight, particularly preferably 0.75 to 4% by weight, and in particular 1 to 2.5% by weight, of xanthan and 0.5 to 30% by weight, preferably 1 to 20% by weight, particularly preferably 5 to 15% by weight, and in particular 6 to 12% by weight, of hydrogen peroxide, calculated as 100% $H_2O_2$. The viscous properties of preparation (B) are important for its good miscibility and high stability. In one preferred embodiment, preparations (B) of the present invention are characterized in that they have a viscosity of 1,000 mPa·s to 50,000 mPa·s, preferably 5,000 mPa·s to 45,000 mPa·s, and particularly preferably 7,000 mPa·s to 40,000 mPa·s, in measurements using a rotary viscometer from Brookfield, spindle size 4, at 25° C. and 4 rpm. The final mixed and ready-to-use agents preferably have a viscosity of 10,000 mPa·s to 50,000 mPa·s, and particularly preferably 18,000 mPa·s to 30,000 mPa·s, in measurements using a rotary viscometer from Brookfield, spindle size 5, at 25° C. and 4 rpm.

In addition, the pH setting is important for good miscibility and stability. Final mixed and ready-to-use agents having a pH between 9 and 12 are preferred according to the invention.

In addition, it may be advantageous according to the invention when preparation (B) includes at least one nonionic surfactant, preferably at least one ethoxylated fatty alcohol having 40 to 60 ethylene oxide units. According to the invention, this is understood to mean an addition product of ethylene oxide with a fatty alcohol. Fatty alcohols are saturated and unsaturated alcohols which contain 12 to 24 C atoms and which may be linear or branched. The molar quantity of ethylene oxide which has been used per mole of fatty alcohol is understood as the ethoxylation number. Suited in particular as nonionic surfactants are ethylene oxide addition products with octyl alcohol (capryl alcohol), nonyl alcohol (pelargonyl alcohol), undecyl alcohol, undec-10-en-1-ol, dodecyl alcohol (lauryl alcohol), 2,6,8-trimethyl-4-nonanol (isolauryl alcohol), tridecyl alcohol, tetradecyl alcohol (myristyl alcohol), pentadecyl alcohol, hexadecyl alcohol (cetyl/palmityl alcohol), heptadecyl alcohol, octadecyl alcohol (stearyl alcohol), isostearyl alcohol, (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenyl alcohol), nonadecan-1-ol (nonadecyl alcohol), eicosan-1-ol (eicosyl alcohol/arachidyl alcohol), (9Z)-eicos-9-en-1-ol (gadoleyl alcohol), (5Z,8Z,11Z,14Z)-eicosa-5,8,11,14-tetraen-1-ol (arachidonic alcohol), heneicosyl alcohol, docosyl alcohol (behenyl alcohol), (13Z)-docos-13-en-1-ol (erucyl alcohol), or (13E)-docosen-1-ol (brassidyl alcohol). It is likewise possible according to the invention to use mixtures of fatty alcohols which result from targeted mixing or also from extraction processes per se. Examples are coco alcohol (mixture of $C_8$-$C_{18}$ fatty alcohols) or cetearyl alcohol (1:1 mixture of $C_{16}$ and $C_{18}$ fatty alcohols).

Ethoxylation numbers of 20 to 60 are preferred. Nonionic surfactants of the ethoxylated fatty alcohol type which are preferred according to the invention are Ceteareth-20 and Ceteareth-50.

In addition, the bleaching agents may contain alkalizing agents. Examples of preferred alkalizing agents include ammonia, alkanolamines, basic amino acids, and inorganic alkalizing agents such as alkali (alkaline earth) metal hydroxides, alkali (alkaline earth) metal metasilicates, alkali (alkaline earth) metal phosphates, and alkali (alkaline earth) metal hydrogen phosphates. Lithium, sodium, and/or potassium is/are preferably used as metal ions. Ammonia is a particularly preferred alkalizing agent. Inorganic alkalizing agents which are usable according to the invention are preferably selected from sodium hydroxide, potassium hydroxide, calcium hydroxide, barium hydroxide, sodium phosphate, potassium phosphate, sodium silicate, potassium silicate, magnesium silicate, sodium carbonate, and potassium carbonate. Sodium hydroxide and/or potassium hydroxide is/are particularly preferred.

Alkalizing agents which are usable according to the invention are preferably selected from alkanolamines and primary, secondary, or tertiary amines having a $C_2$-$C_6$ alkyl base body which bears at least one hydroxyl group. Particularly preferred alkanolamines are selected from the group comprising 2-aminoethan-1-ol (monoethanolamine), 3-aminopropan-1-ol, 4-aminobutan-1-ol, 5-aminopentan-1-ol, 1-aminopropan-2-ol (monoisopropanolamine), 1-aminobutan-2-ol, 1-aminopentan-2-ol, 1-aminopentan-3-ol, 1-aminopentan-4-ol, 2-amino-2-methylpropanol, 2-amino-2-methylbutanol, 3-amino-2-methylpropan-1-ol, 1-amino-2-methylpropan-2-ol, 3-aminopropane-1,2-diol, 2-amino-2-methylpropane-1,3-diol, 2-amino-2-ethyl-1,3-propanediol, N,N-dimethylethanolamine, methylglucamine, triethanolamine, diethanolamine, and triisopropanolamine. Monoethanolamine, 2-amino-2-methyl-propanol, and triethanolamine are particularly preferred alkanolamines.

The basic amino acids which are usable as an alkalizing agent according to the invention are preferably selected from the group comprising L-arginine, D-arginine, D/L-arginine, L-lysine, D-lysine, D/L-lysine, L-ornithine, D-ornithine, D/L-ornithine, L-histidine, D-histidine, and/or D/L-histidine. L-Arginine, D-arginine, and/or D/L-arginine is/are particularly preferably used as an alkalizing agent within the meaning of the invention.

Many customers find the intense odor of ammonia to be annoying or bothersome. Although ammonia is a preferred alkalizing agent, ready-to-use preparations which are free of ammonia may therefore be preferred according to the invention. Monoethanolamine, 2-amino-2-methylpropanol, and triethanolamine are preferred alkalizing agents for preparations that are free of ammonia.

When the ready-to-use mixtures contain alkalizing agent, preparations according to the invention are preferred which contain alkalizing agent in a quantity of 0.05 to 20% by weight, in particular 0.5 to 10% by weight, in each case based on the total weight of the ready-to-use agent.

In another embodiment of the invention, preparations (A) and (B) may be mixed with further separately packaged preparations immediately prior to application to form an application mixture.

In one preferred embodiment of the invention, the agent according to the invention additionally includes at least one further preparation (C) which is packaged separately from preparations (A) and (B), wherein preparation (C) includes at least one alkalizing agent and at least one natural polymer. Preparation (C) preferably includes natural polymers which have already been mentioned in the text above in conjunction with preparation (B).

Alkalizing agents which have already been described above are preferred according to the invention. When the preparations (C) contain alkalizing agent, preparations are preferred according to the invention which contain alkalizing agent in a quantity of 0.05 to 20% by weight, in particular 0.5 to 10% by weight, in each case based on the total weight of the ready-to-use agent.

Regardless of whether preparations (C) and/or preparation (B) and/or further preparations contain(s) alkalizing agent, when alkalizing agents are used, preparations are preferred according to the invention which contain alkalizing agent in a quantity of 0.05 to 20% by weight, in particular 0.5 to 10% by weight, in each case based on the total weight of the ready-to-use agent.

For further increasing the lightening power, a silicon-containing compound may additionally be added to preparation (C) as a bleach enhancer. The silicon-containing compound is preferably selected from the group comprising silicic acid, alkali metal silicates, and alkaline earth metal silicates.

Although even small quantities of the silicon-containing compounds increase the lightening power, it may be preferred according to the invention to use the silicon-containing compounds in quantities of 0.05% by weight to 50% by weight, preferably in quantities of 0.5% by weight to 30% by weight, and particularly preferably in quantities of 1.0% by weight to 25% by weight, in each case based on the total weight of preparation (C).

In particular alkali metal silicates in the form of water glass are used as silicon-containing compounds. Water glass is understood to mean a compound that is formed from a silicate of formula $(SiO_2)_n(Na_2O)_m(K_2O)_p$, where n stands for a positive rational number and m and p independently stand for a positive rational number or for 0, with the condition that at least one of the parameters m or p is different from 0, and the ratio of n to the sum of m and p is between 1:1 and 4:1.

In addition to the components described by the empirical formula, the water glasses may contain further additives, such as phosphates or magnesium salts, in small quantities.

Water glasses which are particularly preferred according to the invention are marketed, among others, under the names Ferrosil® 119, Natronwasserglas 40/42, Portil® A, Portil® AW, and Portil® W, and Britesil® C20.

Furthermore, in particular silicic acids, also marketed as silica or silica gel, may be used as silicon-containing compounds. A silica gel marketed under the trade name Aerosil 200 (INCI name: Silica) is preferred.

In addition, the lightening or bleaching agents may contain additional bleach enhancers for increasing the bleaching effect. Compounds which under perhydrolysis conditions result in aliphatic peroxocarboxylic acids preferably containing 1 to 10 C atoms, in particular 2 to 4 C atoms, and/or optionally substituted perbenzoic acid, may be used as bleach enhancer. Preferred are multiply acylated alkylenediamines, in particular tetraacetylethylenediamine (TAED), acylated triazine derivatives, in particular 1,5-diacetyl-2,4-dioxohexahydro-1,3,5-triazine (DADHT), acylated glycolurils, in particular tetraacetyl glycoluril (TAGU), N-acylimides, in particular N-nonanoyl succinimide (NOSI), acylated phenol sulfonates, in particular n-nonanoyl or isononanoyl oxybenzene sulfonate (n- or iso-NOBS) carboxylic acid anhydrides, in particular phthalic acid anhydride, acylated polyhydric alcohols, in particular triacetin, ethylene glycol diacetate, and 2,5-diacetoxy-2,5-dihydrofuran.

Carbonate salts or hydrogen carbonate salts may preferably be used as bleach enhancers of the carboxylic acid derivative type. These are preferably selected from the group of ammonium, alkali metal (in particular Na and K), and alkaline earth metal (in particular Mg and Ca) carbonate salts or hydrogen carbonate salts. Particularly preferred carbonate salts or hydrogen carbonate salts are ammonium hydrogen carbonate, ammonium carbonate, sodium hydrogen carbonate, sodium carbonate, potassium hydrogen carbonate, potassium carbonate, magnesium carbonate, and calcium carbonate. These particularly preferred salts may be used as bleach enhancer, alone or in mixtures thereof of at least two representatives. In addition, alkyl carbonates, alkyl carbamates, silyl carbonates, and silyl carbamates are suitable bleach enhancers. Furthermore, bleach enhancers which are usable according to the invention may be selected from nitrogen-containing, optionally cationic, heterocycles, in particular imidazole. Particularly preferred nitrogen-containing heterocyclic bleach enhancers are the quaternized cations of pyridines and 3,4-dihydroisoquinolines, such as salts of 4-acetyl-1-methylpyridinium, in particular 4-acetyl- 1-methylpyridinium-p-toluene sulfonate, salts of 2-acetyl-1-methylpyridinium, in particular 2-acetyl-1-methylpyridinium-p-toluene sulfonate, and salts of N-methyl-3,4-dihydroisoquinolinium, in particular N-methyl-3,4-dihydroisoquinolinium-p-toluene sulfonate.

Another bleach enhancer which is usable according to the invention is urea.

Bleach enhancers may be contained in preparation (A) and/or preparation (B) and/or optionally preparation (C) and/or optionally further preparations. The bleach enhancers may be contained either in only one of the preparations, or in two or more of the preparations. Hydrolysis-sensitive bleach enhancers may preferably be used in the powdered preparation (A). Regardless of whether bleach enhancers are used in preparation (A) and/or preparation (B) and/or preparation (C) and/or further preparations, when bleach enhancers are used they are preferably contained in quantities of 0.5 to 30% by weight, in particular in quantities of 2 to 20% by weight, in each case based on the total weight of the final mixed bleaching preparation.

In addition, for delustering undesired residual color impressions, in particular in the reddish or bluish range, the lightening or bleaching agents may contain certain direct dyes of the complementary colors. These are dyes which act directly on the hair and which do not require an oxidative process for forming the color. Direct dyes are customarily nitrophenylenediamines, nitroaminophenols, azo dyes, anthraquinones, or indophenols. Direct dyes are known as anionic, cationic, and nonionic direct dyes. The direct dyes are preferably used in each case in a quantity of 0.001 to 2% by weight, based on the overall use preparation.

Preferred anionic direct dyes are the compounds known under the international names or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, Bromophenol Blue, and Tetrabromophenol Blue. Preferred cationic direct dyes are cationic triphenylmethane dyes, for example Basic Blue 7, Basic Blue 26, Basic Violet 2, and Basic Violet 14, aromatic systems substituted with a quaternary nitrogen group, for example Basic Yellow 57, Basic Red 76, Basic Blue 99, Basic Brown 16, and Basic Brown 17, cationic anthraquinone dyes such as HC Blue 16 (Bluequat B), and direct dyes containing a heterocycle having at least one quaternary nitrogen atom, in particular Basic Yellow 87, Basic Orange 31, and Basic Red 51. The cationic direct dyes, marketed under the trademark Arianor, are cationic direct dyes which are likewise preferred according to the invention. In particular nonionic nitro and quinone dyes and neutral azo dyes are suitable as nonionic direct dyes. Preferred nonionic direct dyes are the compounds known under the international names or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and the salts thereof, 2-amino-6-chloro-4-nitrophenol, 4-ethylamino-3-nitrobenzoic acid, and 2-chloro-6-ethylamino-4-nitrophenol. Agents which contain at least one combination of Tetrabromophenol Blue and Acid Red 92 are particularly preferred.

Furthermore, it has proven to be advantageous when the ready-to-use agents contain at least one stabilizer or complex-forming agent. Particularly preferred stabilizers are phenacetin, alkali benzoates (sodium benzoate), and salicylic acid. In addition, all complex-forming agents of the prior art may be used. These may belong to different chemical groups. They are preferably used individually or in a mixture with one another. Complex-forming agents which are preferred according to the invention are nitrogen-containing polycarboxylic acids, in particular EDTA, and phosphonates, preferably hydroxyalkane or aminoalkane phosphonates, and in particular 1-hydroxyethane-1,1-diphosphonate (HEDP) or the di- or tetrasodium salt thereof, and/or ethylenediamine tetramethylene phosphonate (EDTMP) or the hexasodium salt thereof, and/or diethylenetriamine pentamethylene phosphonate (DTPMP) or the hepta- or octasodium salt thereof.

In addition, the agents according to the invention may contain further active substances, auxiliary substances, and additives, for example nonionic polymers such as vinylpyrrolidinone/vinyl acrylate copolymers, polyvinylpyrrolidinone, vinylpyrrolidinone/vinyl acetate copolymers, polyethylene glycols and polysiloxanes; additional silicones such as volatile or nonvolatile, straight-chain, branched, or cyclic, crosslinked or noncrosslinked polyalkylsiloxanes (such as dimethicones or cyclomethicones), polyarylsiloxanes and/or polyalkylarylsiloxanes, in particular polysiloxanes having organofunctional groups, such as substituted or unsubstituted amines (amodimethicones), carboxyl, alkoxy, and/or hydroxyl groups (dimethicone copolyols), linear polysiloxane (A)-polyoxyalkylene (B) block copolymers, grafted silicone polymers; cationic polymers such as quaternized cellulose ethers, polysiloxanes having quaternary groups, dimethyldiallyl ammonium chloride polymers, acrylamide dimethyldiallyl ammonium chloride copolymers, dimethylaminoethyl methacrylate-vinylpyrrolidinone copolymers quaternized with diethyl sulfate, vinylpyrrolidinone-imidazolinium methochloride copolymers, and quaternized polyvinyl alcohol; zwitterionic and amphoteric polymers; anionic polymers, for example polyacrylic acids or crosslinked polyacrylic acids; structurizers such as glucose, maleic acid, and lactic acid, hair conditioning compounds such as phospholipids, for example lecithin and cephalins; fragrance oils, dimethyl isosorbide, and cyclodextrins; fiber structure-improving active substances, in particular mono-, di-, and oligosaccharides such as glucose, galactose, fructose, fruit sugar, and lactose; dyes for coloring the agent; anti-dandruff active substances such as piroctone olamines, zinc omadines, and climbazole; amino acids and oligopeptides, in particular arginine and/or serine; animal- and/or plant-based protein hydrolysates, for example elastin, collagen, keratin, silk, and milk protein hydrolysates, or almond, rice, pea, potato, and wheat protein hydrolysates, and in the form of their fatty acid condensation products or optionally anionically or cationically modified derivatives; light protection agents such as derivatized benzophenones, cinnamic acid derivatives, and triazines; active substances such as panthenol, pantothenic acid, pantolactone, allantoin, pyrrolidinone carboxylic acids and salts thereof, and bisabolol; polyphenols, in particular hydroxycinnamic acids, 6,7-dihydroxycoumarin, hydroxybenzoic acids, catechins, tannins, leucoanthocyanidins, anthocyanidins, flavanones, flavones, and flavonols; ceramides or pseudoceramides;

vitamins, provitamins, and vitamin precursors, in particular of the groups A, $B_3$, $B_5$, $B_6$, C, E, F, and H; plant extracts; swelling agents and penetration agents such as glycerin, propylene glycol monoethyl ether, carbonates, hydrogen carbonates, guanidines, ureas, and primary, secondary, and tertiary phosphates; pearlescence agents such as ethylene glycol mono- and distearate and PEG-3-distearate; pigments, and propellants such as propane-butane mixtures, $N_2O$, dimethyl ether, $CO_2$, and air. Active substances, auxiliary substances, and additives are particularly preferred according to the invention which, in combination with the agent according to the invention, preferably result in a translucent to transparent application mixture.

Those skilled in the art will select these further substances according to the desired properties of the agents. With regard to further optional components and the quantities of these components used, explicit reference is made to relevant handbooks known to those skilled in the art, for example Kh. Schrader, Grundlagen and Rezepturen der Kosmetika [Fundamentals and Formulations of Cosmetics], 2nd Edition, Hüthig Buch Verlag, Heidelberg, 1989. The additional active substances and auxiliary substances are preferably used in the agents according to the invention in each case in quantities of 0.0001 to 10% by weight, in particular 0.0005 to 5% by weight, based on the total weight of the application mixture.

A second subject matter of the invention relates to a method for changing the color of keratinic fibers, in which at least two separately packaged preparations (A) and (B), of which preparation (A) includes at least one persulfate, at least one acrylate polymer, and carboxymethylcellulose, and preparation (B) includes at least one oxidizing agent, are mixed to form an application mixture, which is applied to the fibers and rinsed off after an exposure period, characterized in that i. preparation (A) includes, based on its weight,
     a1) 0 to 3% by weight of keratin hydrolysate(s) and/or
     a2) 0 to 5% by weight of silicone oil(s), with the condition that preparation (A) includes, based on its weight, 0.1 to 6% by weight of compound(s) from the groups a1) and a2).

The ready-to-use agents are prepared immediately prior to application to the hair by mixing the two preparations (A) and (B) and optionally a third preparation (C) and/or further preparations. For ready-to-use agents which are mixed from more than two preparations to form a final application mixture, it may be irrelevant whether initially two preparations are mixed together and subsequently the third preparation is added and mixed in, or whether all preparations are combined together and subsequently mixed. The mixing may take place by stirring in a bowl or cup or by shaking in a closable container. The term "immediately" is understood to mean a period from a few seconds to one hour, preferably to 30 min, in particular to 15 min.

The agents according to the invention are used in a method for lightening keratinic fibers, in particular human hair, in which the agent is applied to the keratin-containing fibers at a temperature of room temperature to 45° C., left on the fibers for an exposure period of 10 to 60 minutes, and subsequently rinsed off with water or washed out with a shampoo.

The exposure period of the ready-to-use lightening agents is preferably 10 to 60 min, in particular 15 to 50 min, particularly preferably 20 to 45 min. During the exposure period of the agent on the fiber, it may be advantageous to assist the lightening operation by supplying heat. Heat may be supplied via an external heat source, such as hot air from a hot air blower, and, in particular for hair lightening on living subjects, also via the body temperature of the subject. In the latter option, the area to be lightened is customarily covered with a hood. An exposure phase at room temperature is likewise in accordance with the invention. The temperature during the exposure period is preferably between 20° C. and 40° C., in particular between 25° C. and 38° C. The lightening agents provide good bleaching and lightening results even at physiologically acceptable temperatures of less than 45° C.

After conclusion of the exposure period, the remaining lightening preparation is rinsed from the hair with water or a cleaning agent. In particular commercially available shampoo may be used as cleaning agent, in which case in particular the cleaning agent may be dispensed with, and the rinsing operation may take place using tap water when the lightening agent has a strong surfactant-containing carrier.

One preferred method is characterized in that the degree of lightening of the keratinic fiber is visually checked during the exposure period without removing the application mixture from the fiber. For this purpose, a ready-to-use, preferably translucent or transparent agent of the first subject matter of the invention is applied to human hair, and the lightening process is assessed one or more times during the exposure period by visual checking, without removing the agent from the fiber. Simplified, continual checking of the decolorizing operation is thus ensured.

Within the meaning of the invention, preparations are "transparent" when, applied in a uniform layer 1 to 3 mm thick, they are clear on a background and can be seen through, so that the human eye is able to recognize and assess the color of the background without clouding. Transparency may also be measured by those skilled in the art, using technical methods. Within the meaning of the invention, preparations are therefore also "transparent" which achieve transmissions of at least 70%, in particular at least 80%, in photometric measurements using a Methrom 662 photometer at 25° C.

Methods which are preferred according to the invention are characterized in that the degree of lightening of the keratinic fiber is checked visually during the exposure period without removing the application mixture from the fiber.

The preferred embodiments of the first subject matter of the invention also apply mutatis mutandis to the second subject matter of the invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An agent for lightening keratinic fibers, comprising at least two separately packaged preparations (A) and (B) and optionally a further preparation (C) packaged separately from (A) and (B), which are mixed immediately prior to application to form a use preparation, wherein i. preparation (A) includes 5 to 60% by weight of at least one persulfate selected from the group consisting of ammonium peroxodisulfate, potassium peroxodisulfate, and sodium peroxodisulfate, at least one acrylate polymer, and 1.0 to 1.75% by weight, based on the weight of preparation (A) of carboxymethylcellulose having a degree of substitution of 0.75 to 0.85 and silicone oil(s) of formula (I)

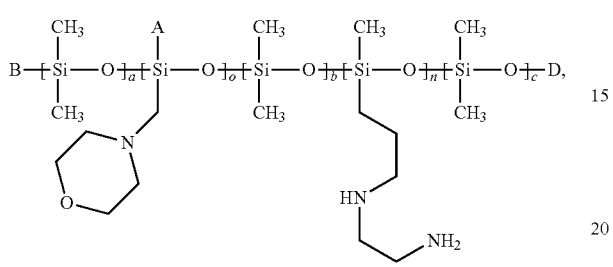

in which
A denotes a structural unit (I), (II) or (III) bound via an —O—

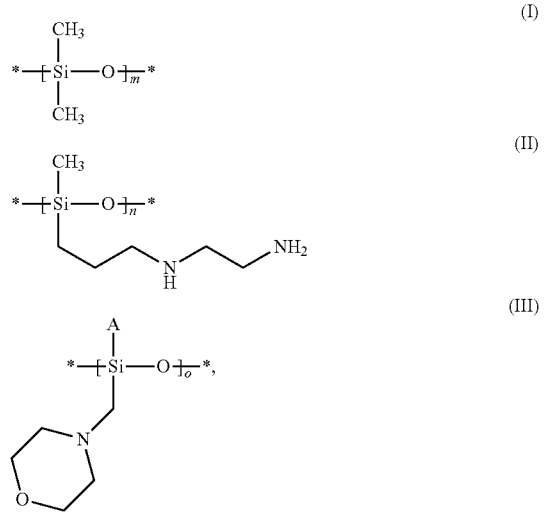

or an oligomeric or polymeric group bound via an —O— and comprising structural units of formulas (I), (II) or (III), or half of a connecting O atom to a structural unit (III), or denotes —OH;
* denotes a bond to one of the structural units (I), (II) or (III) or a terminal group B (Si-bound) or D (O-bound);
B denotes a group —OH, —O—Si(CH$_3$)$_3$, —O—Si (CH$_3$)$_2$OH, —O—Si(CH$_3$)$_2$OCH$_3$;
D denotes a group —H, —Si(CH$_3$)$_3$, —Si(CH$_3$)$_2$OH, —Si(CH$_3$)$_2$OCH$_3$;

a, b and c denote integers between 0 and 1000, with the proviso that a+b+c>0; and
m, n and o denote integers between 1 and 1000, and wherein preparation A is free of xanthan;
ii. preparation (B) is flowable and includes at least one oxidizing agent, 0.01 to 5% by weight of cosmetic oil(s), based on the weight of preparation (B), at least 40% by weight water, and (B), 0.1 to 10% by weight of xanthan and 0.5 to 30% by weight of hydrogen peroxide, calculated as 100% H$_2$O$_2$, each based on the weight of preparation (B),
wherein preparation (A) includes, based on its weight,
a1) 0.01 to 1.0% by weight of keratin hydrolysate(s) having a molar mass of 400 to 1200 Dalton, obtained from the cortex and/or the cuticle of keratinic fibers and
a2) 0.01 to 5% by weight of silicone oil(s) of formula (I),
with the condition that preparation (A) includes, based on its weight, 0.1 to 6% by weight of compound(s) from the groups a1) and a2).

2. The agent according to claim 1, wherein preparation (A) includes 0.05 to 0.75% by weight, by weight, of keratin hydrolysate(s).

3. The agent according to claim 1, wherein preparation (A) comprises 0.1 to 0.5 wt. % wt. % keratin hydrolysate(s).

4. The agent according to claim 1, wherein the silicone oil(s) of formula (I) has/have at least one terminal dimethylsilylhydroxy group, in which
B=—O—Si(CH$_3$)$_2$OH and D=—Si(CH$_3$)$_3$
B=—O—Si(CH$_3$)$_2$OH and D=—Si(CH$_3$)$_2$OH
B=—O—Si(CH$_3$)$_2$OH and D=—Si(CH$_3$)$_2$OCH$_3$
B=—O—Si(CH$_3$)$_3$ and D=—Si(CH$_3$)$_2$OH
B=—O—Si(CH$_3$)$_2$OCH$_3$ and D=—SiCH$_3$)$_2$OH.

5. The agent according to claim 1, wherein the agent includes silicone oil(s) of formula (I) in preparation (A) in which
m>(n+o) or (a+b+c)>(n+o).

6. The agent according to claim 1, further comprising, based on its weight, 0.00001 to 5% by weight branched ethoxylated tridecanol or α-isotridecyl-ω-hydroxypolyglycol ether or the mixtures thereof.

7. A method for changing the color of keratinic fibers, comprising applying to keratinic fibers the agent according to claim 1, and rinsing off the keratinic fibers.

8. The agent according to claim 1, wherein the agent includes silicone oil(s) of formula (I) in preparation (A) in which m>10 (n+o) or (a+b+c)>10 (n+o) applies.

9. The agent according to claim 1, wherein the agent includes silicone oil(s) of formula (I) in preparation (A) in which m>50 (n+o) or (a+b+c)>50 (n+o) applies.

10. The agent according to claim 1, wherein the agent includes silicone oil(s) of formula (I) in preparation (A) in which m>75 (n+o) or (a+b+c)>75 (n+o) applies.

11. The agent according to claim 1, wherein the agent includes silicone oil(s) of formula (I) in preparation (A) in which m>100 (n+o) or (a+b+c)>100 (n+o) applies.

* * * * *